(12) United States Patent
Liang et al.

(10) Patent No.: US 7,649,111 B2
(45) Date of Patent: Jan. 19, 2010

(54) CATALYST FOR THE OXIDATION OF A MIXED ALDEHYDE FEEDSTOCK TO METHACRYLIC ACID AND METHODS FOR MAKING AND USING SAME

(75) Inventors: Wugeng Liang, Katy, TX (US); Scott A. Stevenson, Houston, TX (US); Angie McGuffey, Sugar Land, TX (US); Joseph R. Linzer, Houston, TX (US)

(73) Assignee: Saudi Basic Industries Corporation (SA)

( * ) Notice: Subject to any disclaimer, the term of this patent is extended or adjusted under 35 U.S.C. 154(b) by 464 days.

(21) Appl. No.: 11/189,116

(22) Filed: Jul. 25, 2005

(65) Prior Publication Data

US 2007/0021296 A1 Jan. 25, 2007

(51) Int. Cl.
C07C 51/16 (2006.01)
C07C 51/235 (2006.01)
B01J 27/00 (2006.01)
B01J 27/198 (2006.01)
B01J 27/19 (2006.01)
B01J 27/192 (2006.01)

(52) U.S. Cl. .................. 562/531; 562/532; 562/533; 562/535; 502/208; 502/209; 502/211; 502/212

(58) Field of Classification Search .................. 562/532, 562/531, 533, 535; 502/208, 209, 211, 212
See application file for complete search history.

(56) References Cited

U.S. PATENT DOCUMENTS

| 3,907,712 A | 9/1975 | Ohara et al. ................ 502/243 |
| 3,928,462 A | 12/1975 | Shiraishi et al. ............ 568/480 |
| 3,929,899 A | 12/1975 | Grasselli et al. ............ 568/476 |
| 3,933,751 A | 1/1976 | Callahan et al. ............ 568/477 |
| 3,936,505 A | 2/1976 | Oda et al. ................... 502/215 |
| 3,946,081 A | 3/1976 | Wedemeyer et al. ........ 568/470 |
| 3,954,856 A | 5/1976 | Kobayashi et al. .......... 562/538 |
| 3,956,181 A | 5/1976 | Grasselli et al. ............ 502/212 |
| 3,956,378 A | 5/1976 | Grasselli et al. ............ 562/546 |
| 3,959,384 A | 5/1976 | Takenaka et al. ............ 568/479 |
| 3,963,645 A | 6/1976 | Gelbein ....................... 502/248 |
| 3,966,823 A | 6/1976 | Takenaka et al. ............ 568/479 |
| 3,972,920 A | 8/1976 | Ishii et al. ................... 562/538 |
| 3,980,709 A | 9/1976 | Kubo et al. ................. 568/479 |
| 3,984,477 A | 10/1976 | Kubo et al. ................. 568/479 |
| 3,993,673 A | 11/1976 | McMullen ................... 549/531 |
| 4,001,317 A | 1/1977 | Grasselli et al. ............ 562/546 |
| 4,012,449 A | 3/1977 | Shikakura et al. ........... 568/471 |
| 4,025,565 A | 5/1977 | Oda et al. ................... 568/477 |
| 4,034,008 A | 7/1977 | Kutz et al. .................. 562/546 |
| 4,035,418 A | 7/1977 | Okada et al. ................ 562/538 |
| 4,040,978 A | 8/1977 | Li .............................. 502/212 |
| 4,045,478 A | 8/1977 | Umemura et al. ........... 562/535 |
| 4,049,577 A | 9/1977 | Childress et al. ............ 502/178 |
| 4,052,450 A | 10/1977 | Krabetz et al. .............. 562/546 |
| 4,052,462 A | 10/1977 | Sakakibara et al. .......... 568/477 |
| 4,060,545 A | 11/1977 | Miller et al. ................ 560/208 |
| 4,065,507 A | 12/1977 | Hardman et al. ............ 568/477 |
| 4,066,704 A | 1/1978 | Harris et al. ................ 568/475 |
| 4,078,004 A | 3/1978 | Schlaefer et al. ............ 568/479 |
| 4,087,382 A | 5/1978 | Khoobiar .................... 502/249 |
| 4,111,984 A | 9/1978 | Ishii et al. ................... 562/538 |
| 4,111,985 A | 9/1978 | Okada et al. ................ 562/546 |
| 4,118,419 A | 10/1978 | Ishii et al. ................... 562/534 |
| 4,124,634 A | 11/1978 | Gotoh et al. ................ 562/532 |
| 4,127,603 A | 11/1978 | Bljumberg et al. .......... 562/533 |
| 4,129,600 A | 12/1978 | Childress et al. ............ 568/479 |
| 4,134,859 A | 1/1979 | Kurtz et al. ................. 502/249 |
| 4,148,757 A | 4/1979 | Brazdil et al. ............... 502/205 |
| 4,151,117 A | 4/1979 | Schlaefer .................... 502/212 |
| 4,155,938 A | 5/1979 | Yamamoto et al. .......... 568/479 |
| 4,162,234 A | 7/1979 | Grasselli et al. ............. 502/205 |
| 4,166,808 A | 9/1979 | Daumas et al. ............. 502/249 |
| 4,170,570 A | 10/1979 | Zagata et al. ............... 502/211 |
| 4,171,328 A | 10/1979 | Umemura et al. ........... 568/479 |
| 4,171,454 A | 10/1979 | Miller et al. ................ 562/546 |
| 4,174,354 A | 11/1979 | Grasselli et al. ............. 585/626 |

(Continued)

FOREIGN PATENT DOCUMENTS

| EP | 0 025 715 B1 | 3/1981 |
| EP | 0 169 449 B1 | 1/1986 |
| EP | 0 223 877 B1 | 6/1987 |
| EP | 0 267 556 B1 | 5/1988 |

(Continued)

*Primary Examiner*—Karl E Group
*Assistant Examiner*—Noah S Wiese
(74) *Attorney, Agent, or Firm*—Robert W Strozier; Jim Wheetington

(57) ABSTRACT

A heteropolyacid catalyst for oxidation of isobutyraldehyde, methacrolein or mixtures or combinations thereof to methacrylic acid is disclosed where the heteropolyacid catalyst includes at least molybdenum (Mo), phosphorus (P), vanadium (V), and a first component including bismuth (Bi) and/or boron (B). The heteropolyacid catalyst can also optionally include a second component including potassium (K), rubidium (Rb), cesium (Cs), and/or thallium (Tl) and optionally a third component including antimony (Sb), cerium (Ce), niobium (Nb), indium (In), iron (Fe), chromium (Cr), cobalt (Co), nickel (Ni), manganese (Mn), arsenic (As), silver (Ag), zinc (Zn), germanium (Ge), gallium (Ga), zirconium (Zr), magnesium (Mg), barium (Ba), lead (Pb), tin (Sn), titanium (Ti), aluminum (Al), silicon (Si), tantalum (Ta), tungsten (W), and/or lanthanum (La). The heteropolyacid catalyst can also include an ammonium-containing compound designed to increase a value of medium pores in the final heteropolyacid catalyst. A method for oxidizing isobutanal to methacrylic acid using the heteropolyacid catalyst is also disclosed.

65 Claims, No Drawings

U.S. PATENT DOCUMENTS

| | | | |
|---|---|---|---|
| 4,174,459 A | 11/1979 | Sakamoto et al. | 562/534 |
| 4,176,234 A | 11/1979 | Grasselli et al. | 562/546 |
| 4,180,678 A | 12/1979 | Wada et al. | 562/534 |
| 4,182,907 A | 1/1980 | Grasselli et al. | 562/546 |
| 4,184,981 A | 1/1980 | Vanderspurt | 502/209 |
| 4,186,152 A | 1/1980 | Yamamoto et al. | 568/477 |
| 4,190,608 A | 2/1980 | Grasselli et al. | 562/546 |
| 4,195,187 A | 3/1980 | Vanderspurt | 562/545 |
| 4,205,181 A | 5/1980 | Murib | 560/241 |
| 4,208,303 A | 6/1980 | Sasaki et al. | 502/38 |
| 4,209,640 A | 6/1980 | Yamamoto et al. | 562/532 |
| 4,212,767 A | 7/1980 | Daniel | 502/211 |
| 4,217,309 A | 8/1980 | Umemura et al. | 568/477 |
| 4,219,670 A | 8/1980 | Okada et al. | 562/546 |
| 4,224,187 A | 9/1980 | Vanderspurt | 502/212 |
| 4,224,193 A | 9/1980 | Vanderspurt | 502/307 |
| 4,225,466 A | 9/1980 | Wada et al. | 502/209 |
| 4,230,639 A | 10/1980 | Khoobiar | 568/471 |
| 4,230,640 A | 10/1980 | Khoobiar | 568/477 |
| 4,240,931 A | 12/1980 | Milberger et al. | 502/306 |
| 4,245,118 A | 1/1981 | Yamamoto et al. | 562/532 |
| 4,248,803 A | 2/1981 | Vanderspurt | 568/477 |
| 4,250,339 A | 2/1981 | Sakamoto et al. | 568/471 |
| 4,252,683 A | 2/1981 | Khoobiar | 502/211 |
| RE30,545 E | 3/1981 | Khoobiar | 502/249 |
| 4,258,217 A | 3/1981 | Aoshima et al. | 568/474 |
| 4,261,858 A | 4/1981 | Khoobiar | 502/211 |
| 4,267,385 A | 5/1981 | Umemura et al. | 568/479 |
| 4,267,386 A | 5/1981 | Vanderspurt | 568/480 |
| 4,271,040 A | 6/1981 | Khoobiar | 502/211 |
| 4,272,408 A | 6/1981 | Daniel | 502/211 |
| 4,272,637 A | 6/1981 | Yamamoto et al. | 568/780 |
| 4,276,196 A | 6/1981 | Dalton et al. | 502/212 |
| 4,280,928 A | 7/1981 | Kirch et al. | 502/205 |
| 4,280,929 A | 7/1981 | Shaw et al. | 502/215 |
| 4,292,203 A | 9/1981 | Milberger et al. | 502/304 |
| 4,297,247 A | 10/1981 | Krabetz et al. | 502/310 |
| 4,298,763 A | 11/1981 | Engelbach et al. | 568/479 |
| 4,303,550 A | 12/1981 | Callahan et al. | 502/24 |
| 4,306,088 A | 12/1981 | Nakamura et al. | 568/471 |
| 4,306,090 A | 12/1981 | Kirch et al. | 568/481 |
| 4,311,611 A | 1/1982 | Sasaki et al. | 502/22 |
| 4,316,856 A | 2/1982 | Guttmann et al. | 558/322 |
| 4,320,227 A | 3/1982 | Matsumoto et al. | 562/534 |
| 4,321,160 A | 3/1982 | Farrington et al. | 502/209 |
| 4,323,703 A | 4/1982 | Grasselli et al. | 562/546 |
| 4,332,971 A | 6/1982 | Dalton et al. | 568/480 |
| 4,337,364 A | 6/1982 | Solomon | 568/475 |
| 4,339,355 A | 7/1982 | Decker et al. | 502/343 |
| 4,341,900 A | 7/1982 | Ishii et al. | 562/532 |
| 4,351,963 A | 9/1982 | Ray et al. | 568/477 |
| 4,354,044 A | 10/1982 | Aoshima et al. | 568/479 |
| 4,356,316 A | 10/1982 | Aoshima et al. | 560/208 |
| RE31,088 E | 11/1982 | Grasselli et al. | 562/535 |
| 4,370,490 A | 1/1983 | Gruber et al. | 560/214 |
| 4,374,759 A | 2/1983 | Khoobiar | 502/249 |
| 4,377,501 A | 3/1983 | Khoobiar | 502/211 |
| 4,380,664 A | 4/1983 | Ishii et al. | 562/546 |
| 4,388,223 A | 6/1983 | Ferlazzo et al. | 502/211 |
| 4,388,225 A | 6/1983 | Solomon | 502/346 |
| 4,397,771 A | 8/1983 | Grasselli et al. | 502/306 |
| 4,404,397 A | 9/1983 | Daniel | 562/546 |
| 4,413,147 A | 11/1983 | Khoobiar | 568/476 |
| 4,414,134 A | 11/1983 | Friedrich et al. | 502/204 |
| 4,415,482 A | 11/1983 | Ebner | 502/205 |
| 4,419,270 A | 12/1983 | Ueshima et al. | 502/209 |
| 4,424,141 A | 1/1984 | Grasselli et al. | 502/205 |
| 4,425,255 A | 1/1984 | Toyoda et al. | 502/38 |
| 4,442,308 A | 4/1984 | Arntz et al. | 568/480 |
| 4,443,555 A | 4/1984 | Callahan et al. | 502/211 |
| 4,443,556 A | 4/1984 | Aoki et al. | 502/212 |
| 4,444,906 A * | 4/1984 | Callahan et al. | 502/211 |
| 4,444,907 A | 4/1984 | Ohdan et al. | 502/211 |
| 4,446,328 A | 5/1984 | Aoshima et al. | 568/479 |
| 4,453,006 A | 6/1984 | Shaw et al. | 562/545 |
| 4,454,346 A | 6/1984 | Khoobiar | 562/535 |
| 4,467,113 A | 8/1984 | Matsumoto et al. | 562/535 |
| 4,471,061 A | 9/1984 | Shaw et al. | 502/34 |
| 4,471,062 A | 9/1984 | Farrington et al. | 502/34 |
| 4,479,013 A | 10/1984 | Khoobiar | 568/479 |
| 4,489,170 A | 12/1984 | Krabetz et al. | 502/211 |
| 4,499,301 A | 2/1985 | Murib | 562/546 |
| 4,503,247 A | 3/1985 | Khoobair | 562/535 |
| 4,511,671 A | 4/1985 | Saito et al. | 502/242 |
| 4,518,523 A | 5/1985 | Blum et al. | 502/209 |
| 4,528,398 A | 7/1985 | Callahan et al. | 562/534 |
| 4,530,916 A | 7/1985 | Matsumoto et al. | 502/209 |
| 4,532,365 A | 7/1985 | Khoobiar | 568/479 |
| 4,535,188 A | 8/1985 | Khoobiar | 568/479 |
| 4,537,874 A | 8/1985 | Sato et al. | 502/311 |
| 4,537,998 A | 8/1985 | Shum et al. | 568/483 |
| 4,547,588 A | 10/1985 | Khoobiar | 562/535 |
| 4,552,860 A | 11/1985 | Murib | 502/242 |
| 4,556,731 A | 12/1985 | Guttmann et al. | 562/546 |
| 4,558,028 A * | 12/1985 | Tsuneki et al. | 502/211 |
| 4,558,029 A | 12/1985 | Paparizos et al. | 502/211 |
| 4,558,154 A | 12/1985 | Shum et al. | 562/537 |
| RE32,082 E | 2/1986 | Khoobiar | 568/476 |
| 4,585,883 A | 4/1986 | Briggs | 556/42 |
| 4,596,784 A | 6/1986 | Kennelly et al. | 502/209 |
| 4,621,155 A | 11/1986 | Ueshima et al. | 562/534 |
| 4,652,673 A | 3/1987 | Matsumoto et al. | 562/535 |
| 4,677,084 A | 6/1987 | Bergna | 502/8 |
| 4,720,575 A | 1/1988 | Gruber | 560/214 |
| 4,732,884 A | 3/1988 | Sarumaru et al. | 502/205 |
| 4,778,930 A | 10/1988 | Grasselli et al. | 568/477 |
| 4,803,190 A | 2/1989 | Sarumaru et al. | 502/205 |
| 4,816,603 A | 3/1989 | Oh-Kita et al. | 562/538 |
| 4,855,275 A | 8/1989 | Suresh et al. | 502/353 |
| 4,871,700 A | 10/1989 | Uchida et al. | 502/51 |
| 4,916,103 A | 4/1990 | Martan et al. | 502/212 |
| 4,925,823 A | 5/1990 | Krabetz et al. | 502/211 |
| 4,946,819 A | 8/1990 | Sasaki et al. | 502/214 |
| 4,954,650 A | 9/1990 | Abe et al. | 562/534 |
| 4,968,846 A | 11/1990 | Kuragano et al. | 568/479 |
| 4,985,592 A | 1/1991 | Ishii et al. | 562/534 |
| 5,017,542 A | 5/1991 | Martan et al. | 502/209 |
| 5,059,573 A | 10/1991 | Sasaki et al. | 502/205 |
| 5,072,052 A | 12/1991 | Boeck et al. | 568/479 |
| 5,081,314 A | 1/1992 | Kissel et al. | 568/479 |
| 5,082,819 A | 1/1992 | Boeck et al. | 502/212 |
| 5,094,990 A | 3/1992 | Sasaki et al. | 502/214 |
| 5,102,847 A | 4/1992 | Yamamoto et al. | 502/209 |
| 5,132,269 A | 7/1992 | Sasaki et al. | 502/205 |
| 5,138,100 A | 8/1992 | Matsuura | 568/474 |
| 5,139,988 A | 8/1992 | Sasaki et al. | 502/206 |
| 5,144,090 A | 9/1992 | Honda et al. | 568/476 |
| 5,153,162 A | 10/1992 | Kurimoto et al. | 502/209 |
| 5,155,262 A | 10/1992 | Etzkorn et al. | 562/532 |
| 5,166,119 A | 11/1992 | Oh-Kita et al. | 502/205 |
| 5,173,468 A | 12/1992 | Boehning et al. | 502/209 |
| 5,183,936 A | 2/1993 | Etzkorn et al. | 562/532 |
| 5,198,578 A | 3/1993 | Etzkorn et al. | 562/532 |
| 5,198,581 A | 3/1993 | Kawajiri et al. | 562/546 |
| 5,206,431 A | 4/1993 | Hashiba et al. | 562/534 |
| 5,208,371 A | 5/1993 | Kuroda et al. | 562/534 |
| 5,218,146 A | 6/1993 | Takata et al. | 562/535 |
| 5,221,653 A | 6/1993 | Jaeger et al. | 502/212 |
| 5,221,767 A * | 6/1993 | Boehning et al. | 562/532 |
| 5,225,389 A | 7/1993 | Caillod et al. | 502/205 |
| 5,245,083 A | 9/1993 | Matsuura | 568/479 |
| 5,250,485 A | 10/1993 | Kuroda et al. | 502/159 |
| 5,264,627 A | 11/1993 | Tazaki et al. | 562/599 |
| 5,276,178 A | 1/1994 | Onodera et al. | 562/537 |

| | | | | | | |
|---|---|---|---|---|---|---|
| 5,300,707 | A | 4/1994 | Caillod et al. ............... 568/480 | 6,028,220 A | 2/2000 | Wada et al. ................. 562/546 |
| 5,349,092 | A | 9/1994 | Watanabe et al. ........... 568/480 | 6,043,184 A | 3/2000 | Karmakar et al. ........... 502/208 |
| 5,364,825 | A | 11/1994 | Neumann et al. ............ 502/311 | 6,051,736 A * | 4/2000 | Schraut et al. ............... 562/600 |
| 5,380,933 | A | 1/1995 | Ushikubo et al. ............ 562/549 | 6,060,419 A | 5/2000 | Wijesekera et al. ......... 502/208 |
| 5,491,258 | A | 2/1996 | Watanabe et al. ........... 562/538 | 6,069,271 A | 5/2000 | Tanimoto et al. ............ 562/545 |
| 5,532,199 | A | 7/1996 | Watanabe et al. ........... 502/311 | 6,171,571 B1 | 1/2001 | Bedard et al. ............ 423/594.7 |
| 5,602,280 | A | 2/1997 | Nagai et al. ................. 562/546 | 2004/0034249 A1* | 2/2004 | Arnold et al. ............... 562/547 |
| 5,618,974 | A | 4/1997 | Kurimoto et al. ........... 562/532 | | | |
| 5,670,702 | A | 9/1997 | Jackson et al. .............. 560/208 | | | |
| 5,681,790 | A | 10/1997 | Kim et al. .................... 502/164 | | | |
| 5,684,188 | A | 11/1997 | Hefner et al. ................ 562/532 | | | |
| 5,700,752 | A | 12/1997 | Kurimoto et al. ........... 502/311 | | | |
| 5,728,894 | A | 3/1998 | Nagano et al. .............. 568/479 | | | |
| 5,739,391 | A | 4/1998 | Ruppel et al. ................ 562/532 | | | |
| 5,817,865 | A | 10/1998 | Machhammer et al. ..... 560/208 | | | |
| 5,821,390 | A | 10/1998 | Ruppel et al. ................ 568/470 | | | |
| 5,856,259 | A * | 1/1999 | Watanabe et al. ........... 502/305 | | | |
| 5,877,108 | A | 3/1999 | Suresh et al. ................. 502/20 | | | |
| 5,892,108 | A | 4/1999 | Shiotani et al. ............. 562/532 | | | |
| 5,929,275 | A | 7/1999 | Wada et al. .................. 562/545 | | | |
| 5,948,683 | A | 9/1999 | Koermer et al. ............... 436/37 | | | |
| 5,981,804 | A | 11/1999 | Kurimoto et al. ........... 568/479 | | | |
| 5,990,348 | A | 11/1999 | Lyon et al. ................... 562/549 | | | |

FOREIGN PATENT DOCUMENTS

| | | |
|---|---|---|
| EP | 0 279 374 B1 | 8/1988 |
| EP | 0 450 596 B1 | 10/1991 |
| EP | 0 460 932 B1 | 12/1991 |
| EP | 0 501 794 B1 | 9/1992 |
| EP | 0 523 727 B1 | 1/1993 |
| EP | 0 558 028 B1 | 9/1993 |
| EP | 0 563 025 A1 | 9/1993 |
| EP | 0 574 895 A1 | 12/1993 |
| EP | 0 630 879 A1 | 12/1994 |
| EP | 0 685 260 A2 | 12/1995 |
| EP | 0 767 161 A1 | 4/1997 |
| WO | WO 91/08185 | 6/1991 |

* cited by examiner

CATALYST FOR THE OXIDATION OF A MIXED ALDEHYDE FEEDSTOCK TO METHACRYLIC ACID AND METHODS FOR MAKING AND USING SAME

BACKGROUND OF THE INVENTION

1. Field of the Invention

The present invention relates to a heteropolyacid catalyst including at least molybdenum (Mo), phosphorus (P), vanadium (V), and a first component selected from the group consisting of bismuth (Bi), boron (B) and mixtures or combinations thereof used in producing methacrylic acid by the gas-phase catalytic oxidation of an aldehyde or a mixture of aldehydes, and methods for making and using same.

More particularly, the present invention relates to a heteropolyacid catalyst including molybdenum (Mo), phosphorus (P), vanadium (V), and a first component selected from the group consisting of bismuth (Bi), boron (B) and mixtures or combinations thereof, where the catalyst is adapted to produce methacrylic acid by the gas-phase catalytic oxidation of an aldehyde feedstock including isobutanal (isobutyraldehyde) or isobutanal and methacrolein mixtures. The catalyst can also include copper (Cu). The catalyst can also include a second component selected from the group consisting of potassium (K), rubidium (Rb), cesium (Cs), thallium (Tl), and mixtures or combinations thereof. The catalyst can also include a third component selected from the group consisting of antimony (Sb), cerium (Ce), niobium (Nb), indium (In), iron (Fe), chromium (Cr), cobalt (Co), nickel (Ni), manganese (Mn), arsenic (As), silver (Ag), zinc (Zn), germanium (Ge), gallium (Ga), zirconium (Zr), magnesium (Mg), barium (Ba), lead (Pb), tin (Sn), titanium (Ti), aluminum (Al), silicon (Si), tantalum (Ta), tungsten (W), lanthanum (La), and mixtures or combinations thereof. The invention also relates to methods for making and using same.

2. Description of the Related Art

Isobutanal (isobutyraldehyde) is an intermediate of a process for production of methacrylic acid from propylene. Isobutyraldehyde is formed from the reaction of propylene, carbon monoxide and hydrogen, then oxidation of isobutyraldehyde produces methacrylic acid.

Isobutyraldehyde is also a by-product of 2-ethyl-hexanol production. In this process, propylene is hydroformylated to a mixture of n-butanal (n-butyraldehdye) and isobutanal (isobutyraldehyde). N-butanal is then converted to 2-ethyl-hexanol via base catalyzed oxidation and hydrogenation. Isobutanal is left as a by-product.

Nippon Shokubai has several patents on isobutyraldehyde oxidation. In U.S. Pat. No. 4,558,028, a catalyst for the oxidation of isobutyraldehyde was disclosed having a formula $Mo_{12}P_{1.09}V_{1.09}Cs_{1.0}$. In EP1,060,792, a catalyst for the oxidation of isobutyraldehyde was disclosed having $Mo_{12}P_{1.09}V_{1.09}Cu_{0.05}Cs_{1.0}$.

In other patents such as Chinese Pat. No. 1047985A, U.S. Pat. Nos. 5,153,162 and 5,618,974, arsenic was added as a catalytic component. However, such a toxic component increases the risk of injury to humans and the environment during catalyst manufacturing and handling.

Although many catalysts for the oxidation of isobutyraldehyde to methacrylic acid have been disclosed, there is still a need in the art for alternative highly active, less toxic catalysts for that conversion, especially a catalyst capable of converting an aldehyde feedstock that may include isobutanal alone or a mixture of isobutanal and methacrolein.

DEFINITIONS AND ABBREVIATIONS

The term IBA means isobutanal, sometimes also referred to as isobutyraldehyde.
The term MAC means methacrolein.
The term MAA means methacryclic acid.
The term T means temperature.
The term P means pressure.
The term HC means hydrocarbon.
The term aldehyde feedstock means a stream including mixtures of isobutanal and methacrolein.
The term GC means gas chromatography.
The term FID means flame ionization detector of a GC.
The term h or hr or hrs means hours.
The term g means grams.
The term mL means milliliter.
The term min or min. means minutes.
The term wt % or wt. % means weight percent.
The term vol % or vol. % means volume percent.
The term DI water means deionized water.
The term pore volume distribution means a desired concentration of small pores, medium pores and large pores.
The term small pores means pores having a diameter D less than about 100 Å, i.e., D<100 Å.
The term medium pores means pores having a diameter D greater than or equal to about 100 Å and less than about 1000 Å, i.e., 100 Å<D<1000 Å.
The term large pore volume means pores having a diameter D greater than or equal to about 1000 Å, i.e., D≧1000 Å.

SUMMARY OF THE INVENTION

Catalysts

The present invention provides a novel, highly active, heteropolyacid catalyst including at least molybdenum (Mo), phosphorus (P), vanadium (V), and a first component selected from the group consisting of bismuth (Bi), boron (B) and mixtures or combinations thereof, where the catalyst is capable of converting an aldehyde feedstock into methacrylic acid.

The present invention provides a novel, highly active, heteropolyacid catalyst including at least molybdenum (Mo), phosphorus (P), vanadium (V), and a first component selected from the group consisting of bismuth (Bi), boron (B) and mixtures or combinations thereof, and a second component selected from the group consisting of potassium (K), rubidium (Rb), cesium (Cs), thallium (Tl), and mixtures or combinations thereof, where the catalyst is capable of converting an aldehyde feedstock into methacrylic acid.

The present invention provides a novel, highly active, heteropolyacid catalyst including at least molybdenum (Mo), phosphorus (P), vanadium (V), and a first component selected from the group consisting of bismuth (Bi), boron (B) and mixtures or combinations thereof, a second component selected from the group consisting of potassium (K), rubidium (Rb), cesium (Cs), thallium (Tl), and mixtures or combinations thereof and a third component selected from the group consisting of antimony (Sb), cerium (Ce), niobium (Nb), indium (In), iron (Fe), chromium (Cr), cobalt (Co), nickel (Ni), manganese (Mn), arsenic (As), silver (Ag), zinc (Zn), germanium (Ge), gallium (Ga), zirconium (Zr), magnesium (Mg), barium (Ba), lead (Pb), tin (Sn), titanium (Ti), aluminum (Al), silicon (Si), tantalum (Ta), tungsten (W), lanthanum (La), and mixtures or combinations, where the catalyst is capable of converting an aldehyde feedstock into methacrylic acid.

The present invention provides a novel, highly active, heteropolyacid catalyst including at least molybdenum (Mo), phosphorus (P), vanadium (V), copper (Cu) and a first component selected from the group consisting of bismuth (Bi), boron (B) and mixtures or combinations thereof, where the catalyst is capable of converting an aldehyde feedstock into methacrylic acid.

The present invention provides a novel, highly active, heteropolyacid catalyst including at least molybdenum (Mo), phosphorus (P), vanadium (V), copper (Cu), a first component selected from the group consisting of bismuth (Bi), boron (B) and mixtures or combinations thereof and a second component selected from the group consisting of potassium (K), rubidium (Rb), cesium (Cs), thallium (Tl), and mixtures or combinations thereof, where the catalyst is capable of converting an aldehyde feedstock into methacrylic acid.

The present invention provides a novel, highly active, heteropolyacid catalyst including at least molybdenum (Mo), phosphorus (P), vanadium (V), copper (Cu), a first component selected from the group consisting of bismuth (Bi), boron (B) and mixtures or combinations thereof and a third component selected from the group consisting of antimony (Sb), cerium (Ce), niobium (Nb), indium (In), iron (Fe), chromium (Cr), cobalt (Co), nickel (Ni), manganese (Mn), arsenic (As), silver (Ag), zinc (Zn), germanium (Ge), gallium (Ga), zirconium (Zr), magnesium (Mg), barium (Ba), lead (Pb), tin (Sn), titanium (Ti), aluminum (Al), silicon (Si), tantalum (Ta), tungsten (W), lanthanum (La), and mixtures or combinations, where the catalyst is capable of converting an aldehyde feedstock into methacrylic acid.

The present invention provides a novel, highly active, heteropolyacid catalyst including at least molybdenum (Mo), phosphorus (P), vanadium (V), copper (Cu), a first component selected from the group consisting of bismuth (Bi), boron (B) and mixtures or combinations thereof, a second component selected from the group consisting of potassium (K), rubidium (Rb), cesium (Cs), thallium (Tl), and mixtures or combinations thereof and a third component selected from the group consisting of antimony (Sb), cerium (Ce), niobium (Nb), indium (In), iron (Fe), chromium (Cr), cobalt (Co), nickel (Ni), manganese (Mn), arsenic (As), silver (Ag), zinc (Zn), germanium (Ge), gallium (Ga), zirconium (Zr), magnesium (Mg), barium (Ba), lead (Pb), tin (Sn), titanium (Ti), aluminum (Al), silicon (Si), tantalum (Ta), tungsten (W), lanthanum (La), and mixtures or combinations, where the catalyst is capable of converting an aldehyde feedstock into methacrylic acid.

The present invention also provides a novel, highly active catalyst for converting an aldehyde feedstock into methacrylic acid, where the catalyst has the general formula:

$$Mo_{12}P_aV_bCu_cMI_dMII_eMIII_fO_g \quad (I)$$

where:
MI is selected from the group consisting of bismuth (Bi), boron (B) and mixtures or combinations thereof,
MII is selected from the group consisting of potassium (K), rubidium (Rb), cesium (Cs), thallium (Tl), and mixtures or combinations thereof,
MIII is selected from the group consisting of antimony (Sb), cerium (Ce), niobium (Nb), indium (In), iron (Fe), chromium (Cr), cobalt (Co), nickel (Ni), manganese (Mn), arsenic (As), silver (Ag), zinc (Zn), germanium (Ge), gallium (Ga), zirconium (Zr), magnesium (Mg), barium (Ba), lead (Pb), tin (Sn), titanium (Ti), aluminum (Al), silicon (Si), tantalum (Ta), tungsten (W), lanthanum (La), and mixtures or combinations thereof, a is a number having a value between about 0.1 and about 3.5, b is a number having a value between about 0.01 and about 5.0, c is a number having a value between about 0.0 and about 1.5, d is a number having a value between about 0.01 and about 2.0 when MI is Bi, or a value between about 0.01 and about 5.0 when MI is B, and when MI is both Bi and B, then d includes between about 0.01 and about 2.0 of Bi and between about 0.01 and about 5.0 of B, e is a number having a value between about 0.0 and about 5.0, f is a number having a value between about 0.0 and about 5.0, and g is a number having a value representing a sufficient number of oxygen atoms to balance the oxidation state of the catalyst of formula (I).

The present invention also provides a novel, highly active catalyst for converting an aldehyde feedstock into methacrylic acid of the general formula:

$$Mo_{12}P_aV_bCu_cBi_{d1}MII_eMIII_fO_g \quad (II)$$

where:
MII is selected from the group consisting of potassium (K), rubidium (Rb), cesium (Cs), thallium (Tl), and mixtures or combinations thereof,
MIII is selected from the group consisting of antimony (Sb), cerium (Ce), niobium (Nb), indium (In), iron (Fe), chromium (Cr), cobalt (Co), nickel (Ni), manganese (Mn), arsenic (As), silver (Ag), zinc (Zn), germanium (Ge), gallium (Ga), zirconium (Zr), magnesium (Mg), barium (Ba), lead (Pb), tin (Sn), titanium (Ti), aluminum (Al), silicon (Si), tantalum (Ta), tungsten (W), lanthanum (La), and mixtures or combinations thereof, a is a number having a value between about 0.5 and about 3.5, b is a number having a value between about 0.01 and about 5.0, c is a number having a value between about 0.0 and about 1.5, d1 is a number having a value between about 0.01 and about 2.0, e is a number having a value between about 0.0 and about 5.0, f is a number having a value between about 0.0 and about 5.0, g is a number having a value representing a sufficient number of oxygen atoms to balance the oxidation state of the catalyst of formula (II).

The present invention also provides a novel, highly active catalyst for converting an aldehyde feedstock to methacrylic acid of the general formula:

$$Mo_{12}P_aV_bCu_cB_{d2}MII_eMIII_fO_g \quad (III)$$

where:
MII is selected from the group consisting of potassium (K), rubidium (Rb), cesium (Cs), thallium (Tl), and mixtures or combinations thereof,
MIII is selected from the group consisting of antimony (Sb), cerium (Ce), niobium (Nb), indium (In), iron (Fe), chromium (Cr), cobalt (Co), nickel (Ni), manganese (Mn), arsenic (As), silver (Ag), zinc (Zn), germanium (Ge), gallium (Ga), zirconium (Zr), magnesium (Mg), barium (Ba), lead (Pb), tin (Sn), titanium (Ti), aluminum (Al), silicon (Si), tantalum (Ta), tungsten (W), lanthanum (La), and mixtures or combinations thereof, a is a number having a value between about 0.5 and about 3.5, b is a number having a value between about 0.01 and about 5.0, c is a number having a value between about 0.0 and about 1.5, d2 is a number having a value between about 0.01 and about 5.0, e is a number having a value between about 0.0 and about 5.0, f is a number having a value between about 0.0 and about 5.0, and g is a number having a value representing a sufficient number of oxygen atoms to balance the oxidation state of the catalyst of formula (III).

The present invention also provides a novel, highly active catalyst for converting an aldehyde feedstock to methacrylic acid of the general formula:

$$Mo_{12}P_aV_bCu_cBi_{d1}B_{d2}MII_eMIII_fO_g \qquad (IV)$$

where:

MII is selected from the group consisting of potassium (K), rubidium (Rb), cesium (Cs), thallium (Tl), and mixtures or combinations thereof, MIII is selected from the group consisting of antimony (Sb), cerium (Ce), niobium (Nb), indium (In), iron (Fe), chromium (Cr), cobalt (Co), nickel (Ni), manganese (Mn), arsenic (As), silver (Ag), zinc (Zn), germanium (Ge), gallium (Ga), zirconium (Zr), magnesium (Mg), barium (Ba), lead (Pb), tin (Sn), titanium (Ti), aluminum (Al), silicon (Si), tantalum (Ta), tungsten (W), lanthanum (La), and mixtures or combinations thereof, a is a number having a value between about 0.5 and about 3.5, b is a number having a value between about 0.01 and about 5.0, c is a number having a value between about 0.0 and about 1.5, d1 is a number having a value between about 0.01 and about 2.0, d2 is a number having a value between about 0.01 and about 5.0, e is a number having a value between about 0.0 and about 5.0, f is a number having a value between about 0.0 and about 5.0, and g is a number having a value representing a sufficient number of oxygen atoms to balance the oxidation state of the catalyst of formula (IV).

Methods for Preparing Catalysts

The present invention provides a method for preparing a novel, highly active catalyst for converting an aldehyde feedstock to methacrylic acid. The references to moles used in describing the preparation of the catalysts of this invention mean relative molar amounts, e.g., if 1 mole of catalyst is being prepared, the catalyst will have moles of components such that the molar ratio of molybdenum in the catalyst relative to the other components is 12. As another example, to make a catalyst having the formula $Mo_{12}P_aV_bCu_cBi_{d1}B_{d2}MII_eMIII_fO_g$, the number of moles of components used during catalyst preparation will be in a molar ratio of 12:a:b:c:d1:d2:e:f:g.

The method includes the step of forming a first substantially solid free solution of 12 moles of Mo (1 mole of $Mo_{12}$), a moles of P and b moles of V. If Bi is present in the catalyst, then a second substantially solid-free solution containing d1 moles of Bi is prepared and the two solutions are then mixed to form a slurry. If the catalyst does not include Bi but B, then the solution is heated to 95° C. and d2 moles of B are added to the solution. If the catalyst includes e moles of a second component selected from the group consisting of potassium (K), rubidium (Rb), cesium (Cs), thallium (Tl), and mixtures or combinations thereof, the e moles or any portion thereof of the second components can be added to the first solution prior to or after heating, to the second solution if Bi is present or to the resulting slurry prior to or after heating. Preferably, if the second component is cesium, then the cesium is added to the first solution. The e moles or any portion of the second components can also be added after the solution is precipitated or after the precipitate or slurry is dried, but prior to calcining. If the catalyst also includes f moles of a third component selected from the group consisting of antimony (Sb), cerium (Ce), niobium (Nb), indium (In), iron (Fe), chromium (Cr), cobalt (Co), nickel (Ni), manganese (Mn), arsenic (As), silver (Ag), zinc (Zn), germanium (Ge), gallium (Ga), zirconium (Zr), magnesium (Mg), barium (Ba), lead (Pb), tin (Sn), titanium (Ti), aluminum (Al), silicon (Si), tantalum (Ta), tungsten (W), lanthanum (La), and mixtures or combinations thereof, then as with the e moles of the second components, the third components can be added in any portion as set forth above for the second components. To change the pore size distribution of the catalysts of this invention, a desired amount of an ammonium-containing compound can be added to the first solution and/or the second solution. The ammonium-containing compound is then out-gassed under controlled conditions during catalyst calcination to achieve a desired pore size distribution, preferably a distribution high in medium pores. If Bi is included in the catalyst, the second solution can include an amount of nitric acid to produce a nitric acid to $Mo_{12}$ ratio having a value between about 0.1 to 1.0 to greater than 6.0 to 1.0. The solution or slurry is then evaporated to form a dried pre-catalytic material, which is then calcined to form a catalyst of this invention. As stated above, any portion of the second and third components can be added to the dried pre-catalyst material prior to calcining to form the catalyst of this invention. Generally, a mole ratio of the molybdenum-containing compound to the ammonium-containing compound ($Mo:NH_4$) is between about 0.0 to about 20.0 and between about 0.5 to about 20.0 for catalysts regardless of the molybdenum to nitric acid mole ratio. Preferably, the mole ratio is between about 1.0 to about 15.0, and, particularly, the mole ratio is between about 2.0 to about 10.0. Alternatively, a mole ratio of the ammonium-containing compounds to nitric acid ($NH_4:HNO_3$) is between about 0.0 and about 2.0 and between about 0.1 and about 2.0 for catalysts regardless of the molybdenum to nitric acid mole ratio, preferably, between about 0.2 and about 1.8, particularly, between about 0.4 and about 1.6, and more particularly, between about 0.6 and about 1.4 and especially, between about 0.6 and about 1.2.

Methods for Producing Methacrylic Acid

The present invention also provides a method for preparing methacrylic acid including the step of contacting an aldehyde feedstock with a catalyst of this invention to form methacrylic acid, where the aldehyde feedstock comprises isobutanal or mixtures of isobutanal and methacrolein.

DETAILED DESCRIPTION OF THE INVENTION

The inventors have found that a novel, highly active catalyst for the conversion of an aldehyde feedstock into methacrylic acid can be prepared including at least molybdenum (Mo), phosphorus (P), vanadium (V), and a first component selected from the group consisting of bismuth (Bi), boron (B) and mixtures or combinations thereof. The catalyst is adapted to convert an aldehyde feedstock including isobutanal or mixtures of isobutanal and methacrolein into methacrylic acid. Such a catalyst is ideally suited for use in the conversion of feedstock derived from plants that produce methacrolein and/or produce isobutanal purposefully or as a by-product. Thus, the catalysts of this invention are ideally suited for use in facilities that have a source of methacrolein and isobutanal for the production of methacrylic acid. One such facility integrates a methacrylic acid production component and 2-ethylhexanol production component as set forth in co-filed and co-pending United States Patent Application having a Serial No. associated with Express Mail Label No. ER 441453545 US or any other facility that produces isobutanal as an unwanted by-product.

The present invention broadly relates to novel, highly active, heteropolyacid catalysts including at least molybdenum (Mo), phosphorus (P), vanadium (V), and a first component selected from the group consisting of bismuth (Bi), boron (B) and mixtures or combinations thereof, where the catalysts are capable of converting an aldehyde feedstock into methacrylic acid.

The present invention also broadly relates to a method for making such catalysts including the steps of forming a liquid phase including at least molybdenum (Mo), phosphorus (P), and vanadium (V), and a first component selected from the group consisting of bismuth (Bi), boron (B) and mixtures or combinations thereof, where the liquid phase can be aqueous, aqueous/organic mixtures, aqueous/non-aqueous mixtures, non-aqueous or organic. The term organic means a carbon containing solvent, while the term non-aqueous means a non-aqueous solvent that does not contain carbon. The mixture is then dried to form a pre-catalyst composition and then calcined to form a catalyst of this invention. If the catalyst does not include Bi, then the mixture is preferably a solid-free solution prior to initiating precipitation. If the catalyst includes Bi, then Bi is first dissolved to form a second solid-free solution, which is then added to the first solid-free solution of the other ingredients to form a slurry. If the catalyst also includes the second and/or third components, then these components can be added to the mixture, to either solution or to a dried material followed by further drying, but prior to calcining. If the catalyst also includes an ammonium-containing compound, then the dried catalyst is calcined under controlled conditions, where the conditions are sufficient to allow for controlled out-gassing of the ammonium-containing compound to form a desired pore size distribution, which preferably has a high concentration of medium pores.

The present invention also broadly relates to a process for making MAA including the step of contacting an aldehyde feedstock with a catalyst of this invention under catalysis conditions sufficient to convert a desired amount of the aldehydes in the aldehyde feedstock into MAA.

Suitable Reagents

Suitable compounds used for preparation of the catalysts of this invention include, without limitation, metal nitrates, metal carbonates, metal ammonium salts, metal halides, metal oxides, or mixtures or combinations thereof.

Suitable molybdenum components include, without limitation, ammonium paramolybdate, molybdenum trioxide, molybdenum chloride, etc. or mixtures or combinations thereof. The preferred molybdenum component is ammonium paramolybdate.

Suitable vanadium components include, without limitation, ammonium metavanadate, vanadium pentoxide, vanadium chloride, etc. or mixtures or combinations thereof. The preferred vanadium component is ammonium metavanadate.

Suitable phosphorus components include, without limitation, phosphoric acid, ammonium phosphite, etc. or mixtures or combinations thereof. The preferred phosphorus component is phosphoric acid.

Suitable copper components include, without limitation, copper nitrate, copper chloride, etc. or mixtures or combinations thereof. The preferred copper component is copper nitrate.

Suitable bismuth components include, without limitation, bismuth nitrate, bismuth oxide, bismuth chloride, etc. or mixtures or combinations thereof. The preferred bismuth component is bismuth nitrate.

Suitable boron components include, without limitation, boric acid, boric acid salts, boric oxide, borate esters ($B(OH)_x(OR)_y$, where $x+y=3$ and R is a alkyl group), other similar boron species and mixtures or combinations thereof.

Suitable MII components include, without limitation, MII nitrates, MII oxides, MII chlorides, etc. or mixtures or combinations thereof. The preferred MII components are MII nitrates and MII oxides or mixtures or combinations thereof.

Suitable MIII components include, without limitation, MIII nitrates, MIII oxides, MIII chlorides, etc. or mixtures or combinations thereof. The preferred MIII components are MIII nitrates and MIII oxides or mixtures or combinations thereof.

Suitable ammonium-containing compounds for use in this invention include, without limitation, any ammonium compound that undergoes thermal decomposition to volatile components. Exemplary examples of such ammonium-containing compounds include, without limitation, ammonium hydroxide, ammonium nitrate, ammonium chloride, ammonium bromide, ammonium carbonate, ammonium acetate, ammonium formate, ammonium propionate, ammonium butionate, other ammonium salts of carboxylic acids, or mixtures or combinations thereof.

Catalyst Preparation Aspects

With Bi free catalysts, the catalysts of this invention are generally prepared by initiating precipitation of a substantially precipitate free solution by means known in the art, e.g., heating and/or solvent evaporation, where the solution includes appropriate concentrations of desired catalytic components. While the solution preferably is substantially free of precipitates prior to initiating precipitation, the solution can include varying degrees of precipitates during the preparation procedure provided that the precipitates substantially dissolve prior to initiating precipitation. For catalysts of this invention including Bi, a slurry is formed when a substantially solid-free Bi solution is added to a substantially solid-free solution of other ingredients. Other ingredients can be added to the slurry or to the solid after drying followed by further drying, but prior to calcination. The term substantially solid-free means that the amount of precipitate present in the solution is less than 5 wt. %, preferably less than 2.5 wt. %, particularly less than 1 wt. % and especially less than 0.5 wt. %, with the ultimate goal being completely solid-free or precipitate-free.

The present invention relates to improved catalysts for the oxidation of an aldehyde feedstock comprising isobutanal or isobutanal-methacrolein mixtures. The catalyst of this invention can be prepared from precursor solutions acidified with nitric acid in a nitric acid ($HNO_3$) to $Mo_{12}$ mole ratio of about 0.1 to greater than (>) about 6.0. That is, the catalyst can be made from solutions including about 0.1 moles of nitric acid per mole of $Mo_{12}$ to greater than about 6.0 moles nitric acid per mole of $Mo_{12}$. Preferably, the solutions also include a sufficient amount of an ammonium-containing compound such as ammonium hydroxide to adjust the pH to a desired level and to increase a concentration of medium pores in the final catalyst to a relatively high value. The term "relatively high value" is a value of at least about 50% medium pores in one preferred embodiment, a value of at least about 57% medium pores in another preferred embodiment and a value of at least 60% medium pores in another preferred embodiment. Once the pre-catalyst solution is prepared, the components are precipitated as the temperature of the solution is raised and as water is evaporated from the solution.

When Bi is present in the catalysts of this invention, the catalysts of this invention are prepared using a solution of nitric acid ($HNO_3$) and ammonium hydroxide ($NH_4OH$) to dissolve a bismuth component such as bismuth nitrate ($Bi(NO_3)_3$) or other bismuth salts or compounds, prior to adding the bismuth component to a solution of other components to form a slurry. Again, the MII and MIII components can be added in any portions to either solution or to the slurry either before, during or after drying, but prior to calcination. Again, the ammonium hydroxide or other ammonium-containing compound is added to the Bi solution in an amount sufficient to increase a concentration of medium pores in the resulting pore size distribution to a relatively high value. The catalysts of this invention generally have pore size distribution including between about 0.1% and about 10.0% of small pores and between about 55% and about 80% of medium pores, preferably, the catalyst has a pore size distribution including between about 0.5% and about 7.5% of small pores and between about 60% and about 75% of medium pores, and particularly, the catalyst has a pore size distribution including between about 1.0% and about 5.0% of small pores and between about 60% and about 70% of medium pores.

The catalysts of this invention are rendered more or less active by a calcination procedure to which they are subjected. The general calcination protocol is to calcine a dried catalyst at a temperature and for a time sufficient to obtain a catalyst having a desired activity, generally maximized activity, or to obtain a catalyst having the desired pore size distribution. Generally, the calcination temperature is above about 350° C. and the period of time is between about 2 hours and about 24 hours; however, shorter and longer times can be used. Preferably, the calcination protocol also includes a soak step at a soak temperature and for a soak time sufficient to out-gas volatile components and components that form volatile components at high temperature. Particularly important components that produce volatile components during drying, soaking and calcining include nitrates and ammonium salts. The inventors believe that although the amount of nitrate and ammonium ions present in the dried composition is important for producing the desired pore size distribution, the careful control of drying, soaking and calcining conditions is also important in controlling the number of medium pores generated in the final catalyst. If the pre-calcined catalyst is heated too fast, the volatile components have insufficient time to out-gas and the activity of the resulting catalyst is reduced. Thus, by controlling catalyst drying, soaking and calcining, component out-gassing can be substantially completed before the catalyst is subjected to its final calcination temperature. The soak temperature is generally between about 180° C. and about 250° C. and the soak period of time is between about 1 hour and about 8 hours; however, shorter and longer times can be used. The soak step is designed to allow volatile components and components that form volatile components at high temperature to exit the catalyst gradually and not explosively or so rapidly that the catalyst pore distribution is damaged (collapses or produces too many non-medium pores). In laboratory protocols, the protocols include an initial temperature ramp of about 0.25° C./min. to about 0.75° C./min. for a period of time sufficient to raise the temperature to a desired soak step temperature and a final temperature ramp of about 0.25° C./min. to about 0.75° C./min for a period of time sufficient to raise the temperature to a desired calcination step temperature. In commercial catalyst protocols, however, the ramp rates are generally much higher as is well known in the art of commercial catalyst preparation.

The catalyst of the present invention can be used without a carrier, or can be supported on or diluted with an inert carrier. Suitable inert carriers include, without limitation, silicates, silicas, aluminates, aluminas, silica-aluminas, silicon carbide, zirconias, titanias, magnesia, similar oxides or mixtures or combinations thereof.

The catalysts of this invention are ideally suited for producing an unsaturated acid, preferably a conjugated unsaturated acid such as methacrylic acid by gas-phase catalytic oxidation of a vapor or vapor stream including an aldehyde feedstock such as isobutanal or mixtures of isobutanal and methacrolein at a temperature, at a pressure and for a time sufficient to convert the aldehydes in the aldehyde feedstock to methacrylic acid. The vapor stream used to contact the catalysts of the present invention generally includes sufficient amount of aldehyde in the aldehyde feedstock that is converted into an output stream containing a commercial quantity of methacrylic acid. Preferably, the vapor or vapor stream includes from about 1 vol. % to about 20 vol. % of aldehyde in the aldehyde feedstock, and particularly, the vapor or vapor stream includes from about 3 to about 10 vol. % of aldehyde in the aldehyde feedstock. Typically, an aldehyde feed for the preparation of methacrylic acid may also contain large amounts of water and smaller amounts of impurities such as carbon monoxide, carbon dioxide, acetone, acetic acid, acrolein, methacrylic acid, isobutylene and other saturated and unsaturated hydrocarbons, lower saturated aldehydes, etc., but such impurities have substantially no effect on the conversion of the aldehydes to unsaturated acids.

Although the gas-phase catalytic oxidation reaction of an aldehyde feed stock over a catalyst of this invention can be economically performed in the presence of air, one class of preferred oxidizing agents for use in this invention is oxygen-containing gases having a higher oxygen content than air. Another preferred oxidizing agent for use in this invention is pure oxygen. An amount of the oxidizing agent used in the conversion of the aldehyde feedstock to methacrylic acid is set relative to a molar ratio of oxygen to aldehydes in the aldehyde feedstock. Generally, the molar ratio has a value between about 0.3 and about 4.0, preferably, the ratio has a value between about 0.8 and about 3.0. The oxidizing gas may be diluted with or contain an inert gas such as nitrogen, steam, carbon dioxide, etc., recycled oxygen-containing gases or mixtures or combinations thereof.

In producing methacrylic acid using the catalysts of this invention, the oxidation is generally carried out at a reaction pressure between sub-ambient and several atmospheres above ambient, preferably, the pressure is near ambient or as low as practical. The oxidation reaction using the catalysts of this invention is generally carried out at an elevated temperature, preferably, at a temperature between about 230° C. and about 450° C., particularly, at a temperature between about 250° C. and about 400° C. and more particularly, at a temperature between about 250° C. and about 350° C. The oxidation reaction using the catalysts of this invention can be carried out using a variety of reactor systems including a fixed bed reactor (a reactor having one or more fixed catalyst beds or zones), a fluidized bed reactor (recycling catalyst in a gas entrained reaction environment), a moving bed reactor (catalyst moves in and out of the catalyst zone(s)), a continuous stirred tank reactor or any other reactor system geared for carrying out an oxidizing reaction such as the conversion of isobutyraldehyde to methacrylic acid.

EXPERIMENTAL SECTION

General Considerations

The following examples illustrate the preparation, calcination and testing of specific catalytic formulations of this invention and of comparative catalysts. Example 1 illustrates the preparation of a specific catalyst of this invention including both B and Bi, while Comparative Example 1 illustrates the preparation of a catalyst excluding B and Bi. Comparative Example 2 is a known mixed metal oxide isobutanal oxidation catalyst, which converts isobutanal to methacrolein. Comparative Example 3 is a commercially available heteropolyacid catalyst. Comparative Example 2 and Comparative Example 3 are used to compare a catalyst of this invention for converting a mixture of isobutanal and methacrolein to methacrylic acid. The examples also include performance data for catalysts of this invention and the comparative examples.

Catalysts Preparation

EXAMPLE 1

The following example illustrates the preparation of a 50 g batch of a catalyst of this invention having the following formula $Mo_{12}P_{1.5}V_{0.5}Cu_{0.1}Bi_{0.5}Sb_{0.8}Cs_{1.0}B_{0.5}O_g$.

46.49 g of ammonium paramolybdate were added to 200 mL of de-ionized (DI) water at room temperature. 1.28 g of ammonium metavanadate were added to the above solution with mixing at room temperature. The mixture was stirred at room temperature until all particles were dissolved to produce an MoV solution. 4.28 g of cesium nitrate were then added to 25 mL of DI water, and the resulting solution was added to the MoV solution with mixing to form an MoVCs solution. 3.80 g of phosphoric acid were then dissolved in 6 mL of DI water and the resulting solution was added to the MoVCs solution with mixing to form an MoVCsP solution. 0.51 g of copper nitrate were added to 5mL of DI water and the resulting solution was added to the MoVCsP solution with mixing to form an MoVCsPCu solution. 11.32 g of nitric acid were added to 30 grams of DI water, then 7 mL of ammonium hydroxide (28 wt. % solution) were added to the nitric acid solution and then 5.32 g of bismuth nitrate were added to the nitric acid/ammonium hydroxide solution with mixing and the mixture was stirred until the bismuth nitrate went into solution to form a Bi solution. The Bi solution was then added to the MoVCsPCu solution with mixing forming an MoVCsPCuBi slurry. The Bi solution causes a precipitation of the components as it is added to the MoVCsPCu solution or as the MoVCsPCu solution is added to the Bi solution. The resulting MoVCsPCuBi slurry was then heated to 95° C. and then 2.56 g of antimony trioxide and 0.68 g of boric acid were added to the MoVCsPCuBi slurry with mixing to form an MoVCsPCuBiSbB slurry.

The MoVCsPCuBiSbB slurry was then evaporated at about 100° C. to form an evaporated mixture. The evaporated mixture was then dried at about 130° C. for about 16 hours and sieved to obtain particles having a size between about 20 and 30 mesh. The particles were then heated to a soak temperature of 230° C. at a rate of 0.5° C./min and held at the soak temperature for 3 hours in air. The particles were then heated to a calcination temperature of 380° C. at a rate of 0.5° C./min. and held at the calcination temperature for 5 hours in air to form the $Mo_{12}P_{1.5}V_{0.5}Cu_{0.1}Bi_{0.5}Sb_{0.8}Cs_{1.0}O_g$ catalyst.

COMPARATIVE EXAMPLE 1

This example illustrates the preparation of a 50 g batch of a catalyst of this invention having the composition $Mo_{12}P_{1.5}V_{0.5}Cu_{0.1}Sb_{0.8}CS_{1.0}O_g$.

46.49 g of ammonium paramolybdate were added to 200 mL of de-ionized (DI) water at room temperature. 1.28 g of ammonium metavanadate were added to above solution. The mixture was stirred at room temperature until all particles were dissolved. 4.28 g of cesium nitrate were added to 25 mL of DI water, and the solution was added to above mixture. 3.80 g of phosphoric acid were dissolved in 6 mL of DI water and the solution obtained was added to above mixture. 0.51 g of copper nitrate were added to 5 mL of DI water and solution obtained was added into the above mixture. 11.32 g of nitric acid were added to 30 g of DI water, then 7 mL of a 28 wt. % solution of $NH_4OH$ were added into this solution, and the solution obtained was added to the above mixture. The temperature of the mixture was increased to 95° C. Then, 2.56 g of antimony trioxide were added to the above mixture. The mixture was evaporated at 100° C., dried at 130° C. for 16 hours, and sieved to obtain 20-30 mesh particles. The particles were then heated to a soak temperature of 230° C. at a rate of 0.5° C./min and held at the soak temperature for 3 hours in air. The particles were then heated to a calcination temperature of 380° C. at a rate of 0.5° C./min. and held at the calcination temperature for 5 hours in air.

Catalyst Performance Data 6 cc of the Example 1 catalyst was loaded into a fixed bed reactor and diluted with 9 cc of quartz chips. The catalyst was tested with a vapor stream having the following composition: 4 vol. % isobutyraldehyde (IBA), 30 vol. % steam with the balance being nitrogen and having two different oxygen to IBA mole ratios ($O_2$/HC), where the oxygen-containing gas was air. By varying reaction temperature and vapor stream flow rate, conversion and selectivity data were obtained under a variety of conditions. The resulting effluent stream was analyzed by gas chromatography (GC).

To understand the following results, the following definitions are set forth:

% conversion=$[(IBA_i-IBA_f)/IBA_i]*100$

% MAA selectivity=$[(MAA)/(IBA_i-IBA_f)]*100$

% MAC selectivity=$[(MAC)/(IBA_i-IBA_f)]*100$.

To determine the amount of IBA remaining after the reaction, the products were trapped in a Dewar flask at 0° C. Analysis of the liquid collected did not show any trace of IBA.

Based on the accuracy GC flame ionization detector (FID), the conversion of IBA was estimated to be greater than about 95%.

The catalytic results are shown in Table I.

TABLE I

IBA Conversion Performance of the Catalyst of Example 1

| Flow Rate (sccm) | T (° C.) | $O_2$/HC | IBA Conversion (%) | MAC Selectivity (%) | MAA Selectivity (%) | Total Selectivity (%) |
| --- | --- | --- | --- | --- | --- | --- |
| 100 | 280 | 2.0 | 100 | 30.4 | 53.4 | 83.8 |
| 75  | 281 | 2.0 | 100 | 15.5 | 65.1 | 80.6 |
| 64  | 282 | 2.0 | 100 | 13.6 | 62.9 | 76.5 |
| 57  | 282 | 2.0 | 100 | 7.5  | 67.9 | 75.4 |
| 50  | 281 | 2.0 | 100 | 5.9  | 66.7 | 72.6 |
| 100 | 283 | 2.4 | 100 | 28.7 | 54.4 | 83.1 |
| 75  | 282 | 2.4 | 100 | 15.9 | 63.2 | 79.1 |
| 64  | 282 | 2.4 | 100 | 12.6 | 64.5 | 77.1 |
| 57  | 282 | 2.4 | 100 | 7.8  | 66.9 | 74.7 |
| 50  | 282 | 2.4 | 100 | 5.6  | 67.7 | 73.3 |

Total isobutyraldehyde conversion and around 80% combined methacrolein and methacrylic acid selectivity was obtained with the catalyst of Example 1. Changes in a mole ratio ($O_2$:HC) of hydrocarbon (HC) had little effect on reaction results.

The catalyst of Example 1 was also tested for the oxidation of methacrolein. The testing conditions were the same as those described above, except that 4 vol. % of methacrolein was fed instead of the 4 vol. % of IBA. The data obtained are tabulated in Table II.

TABLE II

MAC Conversion Performance of the Catalyst of Example 1

| Flow Rate (sccm) | T (° C.) | $O_2$/HC | MAC Conversion (%) | MAA Selectivity (%) |
| --- | --- | --- | --- | --- |
| 100 | 278 | 2.0 | 78.4 | 85.2 |
| 75  | 279 | 2.0 | 87.4 | 82.0 |
| 64  | 278 | 2.0 | 94.0 | 80.5 |

The error in the conversion data is about ±3%.

The data indicate that the same reaction conditions (reaction temperature and oxygen/hydrocarbon mole ratio) can be used for the oxidation of isobutanal and methacrolein or mixtures or combinations thereof to product methacrylic acid. Thus, the catalysts of this invention can be used to produce methacrylic acid from a stream containing isobutanal or isobutanal-methacrolein mixtures. Generally, the compositional ranges for the aldehyde feedstock for use with the catalysts of this invention range between about 5 wt. % isobutanal and about 95 wt. % methacrolein to about 95 wt. % isobutanal and about 5 wt. % methacrolein. Another preferred mixture of aldehydes has a composition ranging between about 10 wt. % isobutanal and about 90 wt. % methacrolein to about 90 wt. % isobutanal and about 10 wt. % methacrolein. Another preferred mixture of aldehydes has a composition ranging between about 15 wt. % isobutanal and about 85 wt. % methacrolein to about 85 wt. % isobutanal and about 15 wt. % methacrolein. Another preferred mixture of aldehydes has a composition ranging between about 20 wt. % isobutanal and about 80 wt. % methacrolein to about 80 wt. % isobutanal and about 20 wt. % methacrolein. Another preferred mixture of aldehydes has a composition ranging between about 25 wt. % isobutanal and about 75 wt. % methacrolein to about 75 wt. % isobutanal and about 25 wt. % methacrolein. Another preferred mixture of aldehydes has a composition ranging between about 30 wt. % isobutanal and about 70 wt. % methacrolein to about 70 wt. % isobutanal and about 30 wt. % methacrolein. Another preferred mixture of aldehydes has a composition ranging between about 35 wt. % isobutanal and about 65 wt. % methacrolein to about 65 wt. % isobutanal and about 35 wt. % methacrolein. Another preferred mixture of aldehydes has a composition ranging between about 40 wt. % isobutanal and about 60 wt. % methacrolein to about 60 wt. % isobutanal and about 40 wt. % methacrolein. Another preferred mixture of aldehydes has a composition ranging between about 45 wt. % isobutanal and about 55 wt. % methacrolein to about 55 wt. % isobutanal and about 45 wt. % methacrolein. Another preferred mixture of aldehydes has a composition ranging between about 50 wt. % isobutanal and about 50 wt. % methacrolein. The term "about", in the context of this invention, means ±2.5 wt. %. Of course, depending on starting material availability (IBA and MAC), the actual composition of the stream can actually be any composition within the ranges set forth above.

Reaction and Results 6 cc of the catalysts of Example 1 and Comparative Example 1 were loaded in a fixed bed reactor and diluted with 9 cc of quartz chips. Each catalyst was tested using a feed including 4% IBA and 30% steam with the balance being nitrogen in the presence of oxygen at an oxygen to IBA mole ratio of 2 ($O_2$/HC). The products were analyzed by GC. Because IBA is converted to MAA in a two step process going through MAC, the IBA conversion data includes a MAC conversion component as shown in Table III.

To determine the amount of IBA remaining after the reaction, the products were trapped in a Dewar at 0° C. Analysis of the liquid collected did not show any trace of IBA. Based on the accuracy of a GC flame ionization detector (FID), the conversion of IBA was estimated to be greater than about 99.95%.

The catalyst activities and selectivities for catalysts of Example 1 and Comparative Example 1 obtained under the same reaction temperature (281 ° C.) are tabulated in TABLE III:

TABLE III

Comparison between Example 1 and Comparative Example 1

| Catalyst | Flow rate (sccm) | IBA conversion (%) | MAC conversion (%) | MAA selectivity (%) |
| --- | --- | --- | --- | --- |
| Example 1 | 100 | 100 | 74.7 | 83.6 |
|  | 75 | 100 | 84.3 | 78.6 |
|  | 50 | 100 | 94.0 | 71.7 |
| Comparative Example 1 | 100 | 100 | 48.4 | 82.6 |
|  | 75 | 100 | 69.9 | 78.2 |
|  | 50 | 100 | 74.7 | 75.3 |

It can be seen that at the same reaction condition, the catalyst of Example 1 showed higher conversion of methacrolein than the catalyst of Comparative Example 1, and at the same reaction conversion, the catalyst of Example 1 had higher selectivity than the catalyst of Comparative Example 1. Thus, for isobutyradehyde oxidation, the data clearly indicate that catalysts including Bi and B show better performance than catalyst without Bi and B.

COMPARATIVE EXAMPLE 2

This example illustrates the preparation of a catalyst according to Example 1 of U.S. Pat. No. 4,381,411.

40.40 g of $Fe(NO_3)_3$, 13.59 g of $AgNO_3$ and 21.22 g of 85% $H_3PO_4$ were dissolved in 100 mL of water. The resulting solution was evaporated to a dry paste with heating and stirring. Then, after drying and calcining, a catalyst with composition of $Ag_{0.8}FeP_{1.84}O_x$ was obtained.

COMPARATIVE EXAMPLE 3

A sample of the commercially available heteropolyacid catalyst $(NH_4)_3PMoO_{12}$.

Reaction And Results 6 cc of each of the catalysts of Example 1 and Comparative Example 2 and Comparative Example 3 was loaded in a fixed bed reactor and diluted with 9 cc of quartz chips. Each catalyst was tested with a feed of 2% IBA, 2% of MAC, 30% steam with the balance being nitrogen in the presence of oxygen at an oxygen to hydrocarbon mole ratio ($O_2$/HC) of 2. The oxidation reactions were carried out at a reaction temperature of 284° C. and at a feed flow rate of 50 sccm. The products were analyzed by GC.

To determine the isobutyraldehyde left in the products, products after the reaction were trapped in a Dewar at 0° C. Analysis of the liquid collected did not show any trace of isobutyraldehyde. Based on the accuracy of GC detector (FID), the conversion of isobutanal is at least higher than 99.95%.

The reaction results obtained using the catalysts of Example 1, Comparative Example 2 and Comparative Example 3 to convert a 50-50 mixture of IBA and MAC to MAA are tabulated in Table IV.

TABLE IV

Conversion and Selectivity Data for Using IBA/MAC Mixed Feeds

| Catalyst | IBA Conversion (%) | MAC Conversion (%)$^a$ | Selectivity (%) | One pass yield (%) |
|---|---|---|---|---|
| Example 1 | 100.0 | 93.0 | 83.1 | 77.3 |
| Comp. Example 2 | 100.0 | <30 | <30 | <10 |
| Comp. Example 3 | 100.0 | <20 | <20 | <5 |

$^a$MAC Conversion is defined analogously to the definition of IBA Conversion

This data clearly indicate that the catalysts of this invention work for mixtures of IBA and MAC, while the comparative catalysts show much lower performance.

All references cited herein are incorporated by reference. While this invention has been described fully and completely, it should be understood that, within the scope of the appended claims, the invention may be practiced otherwise than as specifically described. Although the invention has been disclosed with reference to its preferred embodiments, from reading this description those of skill in the art may appreciate changes and modification that may be made which do not depart from the scope and spirit of the invention as described above and claimed hereafter.

We claim:

1. A method comprising the step of:
contacting an aldehyde feedstock and an oxidizing agent in the presence of a heteropolyacid catalyst composition comprising at least molybdenum (Mo), phosphorus (P), vanadium (V), and a first component selected from the group consisting of bismuth (Bi), boron (B) and mixtures or combinations thereof to form methacrylic acid, where the aldehyde feedstock comprises isobutanal or a mixture of isobutanol and methacrolein and where the heteropolyacid catalyst composition has a pore size distribution including a relatively high percentage of medium size pores greater than or equal to 50%.

2. The method of claim 1, wherein the aldehyde feedstock comprises a mixture of isobutanal and methacrolein.

3. The method of claim 1, further comprising a second component selected from the group consisting of potassium (K), rubidium (Rb), cesium (Cs), thallium (Tl), and mixtures or combinations thereof.

4. The method of claim 3, further comprising a third component selected from the group consisting of antimony (Sb), cerium (Ce), niobium (Nb), indium (In), iron (Fe), chromium (Cr), arsenic (As), silver (Ag), zinc (Zn), germanium (Ge), gallium (Ga), zirconium (Zr), magnesium (Mg), barium (Ba), lead (Pb), tin (Sn), titanium (Ti), aluminum (Al), silicon (Si), tantalum(Ta), tungsten (W), lanthanum (La), and mixtures or combinations thereof.

5. The method of claim 1, further comprising a second component selected from the group consisting of potassium (K), rubidium (Rb), cesium (Cs), thallium (Tl), and mixtures or combinations thereof and a third component selected from the group consisting of antimony (Sb), cerium (Ce), niobium (Nb), indium (In), iron (Fe), chromium (Cr), cobalt (Co), nickel (Ni), manganese (Mn), arsenic (As), silver (Ag), zinc (Zn), germanium (Ge), gallium (Ga), zirconium (Zr), magnesium (Mg), barium (Ba), lead (Pb), tin (Sn), titanium (Ti), aluminum (Al), silicon (Si), tantalum (Ta), tungsten (W), lanthanum (La), and mixtures or combinations thereof.

6. The method of claim 1, wherein the first component comprises bismuth and boron.

7. The method of claim 1, wherein the relatively high percentage of medium pores is a value between about 50% and about 80%.

8. The method of claim 1, wherein the relatively high percentage of medium pores is a value greater than or equal to 55%.

9. The method of claim 1, wherein the relatively high percentage of medium pores is a value greater than or equal to 60%.

10. The method of claim 1, wherein the heteropolyacid catalyst is prepared using an amount of an ammonium-containing compound sufficient to increase a percentage of medium pores in the heteropolyacid catalyst, where the ammonium-containing compound is selected from the group consisting of any ammonium compound that undergoes thermal decomposition to volatile components.

11. The method of claim 10, wherein the ammonium-containing compound is selected from the group consisting of ammonium hydroxide, ammonium nitrate, ammonium chloride, ammonium bromide, ammonium carbonate, ammonium salts of carboxylic acids, and mixtures or combinations thereof.

12. The method of claim 11, wherein the ammonium salts of carboxylic acids are selected from the group consisting of ammonium acetate, ammonium formate, ammonium propionate, ammonium butionate, and mixtures or combinations thereof.

13. The method of claim 1, where in the heteropolyacid catalyst composition comprises a compound having the general formula:

$$Mo_{12}P_aV_bCu_cMI_dMII_eMIII_fO_g \quad (I)$$

where:
MI is selected from the group consisting of bismuth (Bi), boron (B) and mixtures or combinations thereof,
MII is selected from the group consisting of potassium (K), rubidium (Rb), cesium (Cs), thallium (Tl), and mixtures or combinations thereof,
MIII is selected from the group consisting of antimony (Sb), cerium (Ce), niobium (Nb), indium (In), iron (Fe), chromium (Cr), cobalt (Co), nickel (Ni), manganese (Mn), arsenic (As), silver (Ag), zinc (Zn), germanium (Ge), gallium (Ga), zirconium (Zr), magnesium (Mg), barium (Ba), lead (Pb), tin (Sn), titanium (Ti), aluminum (Al), silicon (Si), tantalum (Ta), tungsten (W), lanthanum (La), and mixtures or combinations thereof,
a is a number having a value between about 0.1 and about 3.5,
b is a number having a value between about 0.01 and about 5.0,
c is a number having a value between about 0.0 and about 1.5,
d is a number having a value between about 0.01 and about 2.0 when MI is Bi, or a value between about 0.01 and about 5.0 when MI is B, and when MI is both Bi and B, then d includes between about 0.01 and about 2.0 of Bi and between about 0.01 and about 5.0 of B,
e is a number having a value between about 0.0 and about 5.0,
f is a number having a value between about 0.0 and about 5.0, and
g is a number having a value representing a sufficient number of oxygen atoms to balance the oxidation state of the heteropolyacid catalyst of formula (I).

14. The method of claim 13, wherein the aldehyde feedstock comprises a mixture of isobutanal and methacrolein.

15. The method of claim 13, wherein the MI comprises a mixture of bismuth and boron.

16. The method of claim 13, wherein the relatively high percentage of medium pores is a value between about 50% and about 80%.

17. The method of claim 13, wherein the relatively high percentage of medium pores is a value greater than or equal to 55%.

18. The method of claim 13, wherein the relatively high percentage of medium pores is a value greater than or equal to 60%.

19. The method of claim 13, wherein the heteropolyacid catalyst is prepared using an amount of an ammonium-containing compound sufficient to increase a percentage of medium pores in the heteropolyacid catalyst, where the ammonium-containing compound is selected from the group consisting of any ammonium compound that undergoes thermal decomposition to volatile components.

20. The method of claim 19, wherein the ammonium-containing compound is selected from the group consisting of ammonium hydroxide, ammonium nitrate, ammonium chloride, ammonium bromide, ammonium carbonate, ammonium salts of carboxylic acids, and mixtures or combinations thereof.

21. The method of claim 20, wherein the ammonium salts of carboxylic acids are selected from the group consisting of ammonium acetate, ammonium formate, ammonium propionate, ammonium butionate, and mixtures or combinations thereof.

22. The method of claim 1, where in the heteropolyacid catalyst composition comprises a compound having the general formula:

$$Mo_{12}P_aV_bCu_cBi_{d1}MII_eMIII_fO_g \quad (II)$$

where:
MII is selected from the group consisting of potassium (K), rubidium (Rb), cesium (Cs), thallium (Tl), and mixtures or combinations thereof,
MIII is selected from the group consisting of antimony (Sb), cerium (Ce), niobium (Nb), indium (In), iron (Fe), chromium (Cr), cobalt (Co), nickel (Ni), manganese (Mn), arsenic (As), silver (Ag), zinc (Zn), germanium (Ge), gallium (Ga), zirconium (Zr), magnesium (Mg), barium (Ba), lead (Pb), tin (Sn), titanium (Ti), aluminum (Al), silicon (Si), tantalum (Ta), tungsten (W), lanthanum (La), and mixtures or combinations thereof,
a is a number having a value between about 0.5 and about 3.5,
b is a number having a value between about 0.01 and about 5.0,
c is a number having a value between about 0.0 and about 1.5,
d1 is a number having a value between about 0.01 and about 2.0,
e is a number having a value between about 0.0 and about 5.0,
f is a number having a value between about 0.0 and about 5.0,
g is a number having a value representing a sufficient number of oxygen atoms to balance the oxidation state of the heteropolyacid catalyst of formula (II).

23. The method of claim 22, wherein the aldehyde feedstock comprises a mixture of isobutanal and methacrolein.

24. The method of claim 22, wherein the relatively high percentage of medium pores is a value between about 50% and about 80%.

25. The method of claim 22, wherein the relatively high percentage of medium pores is a value greater than or equal to 55%.

26. The method of claim 22, wherein the relatively high percentage of medium pores is a value greater than or equal to 60%.

27. The method of claim 22, wherein the heteropolyacid catalyst is prepared using an amount of an ammonium-containing compound sufficient to increase a percentage of medium pores in the heteropolyacid catalyst, where the ammonium-containing compound is selected from the group consisting of any ammonium compound that undergoes thermal decomposition to volatile components.

28. The method of claim 27, wherein the ammonium-containing compound is selected from the group consisting of ammonium hydroxide, ammonium nitrate, ammonium chloride, ammonium bromide, ammonium carbonate, ammonium salts of carboxylic acids, and mixtures or combinations thereof.

29. The method of claim 28, wherein the ammonium salts of carboxylic acids are selected from the group consisting of ammonium acetate, ammonium formate, ammonium propionate, ammonium butionate, and mixtures or combinations thereof.

30. The method of claim 1, where in the heteropolyacid catalyst composition comprises a compound having the general formula:

$$Mo_{12}P_aV_bCu_cB_{d2}MII_eMIII_fO_g \qquad (III)$$

where:
MII is selected from the group consisting of potassium (K), rubidium (Rb), cesium (Cs), thallium (Tl), and mixtures or combinations thereof,
MIII is selected from the group consisting of antimony (Sb), cerium (Ce), niobium (Nb), indium (In), iron (Fe), chromium (Cr), cobalt (Co), nickel (Ni), manganese (Mn), arsenic (As), silver (Ag), zinc (Zn), germanium (Ge), gallium (Ga), zirconium (Zr), magnesium (Mg), barium (Ba), lead (Pb), tin (Sn), titanium (Ti), aluminum (Al), silicon (Si), tantalum (Ta), tungsten (W), lanthanum (La), and mixtures or combinations thereof,
a is a number having a value between about 0.5 and about 3.5,
b is a number having a value between about 0.01 and about 5.0,
d2 is a number having a value between about 0.01 and about 5.0,
e is a number having a value between about 0.0 and about 5.0,
f is a number having a value between about 0.0 and about 5.0, and
g is a number having a value representing a sufficient number of oxygen atoms to balance the oxidation state of the heteropolyacid catalyst of formula (III).

31. The method of claim 30, wherein the aldehyde feedstock comprises a mixture of isobutanal and methacrolein.

32. The method of claim 30, wherein the relatively high percentage of medium pores is a value between about 50% and about 80%.

33. The method of claim 30, wherein the relatively high percentage of medium pores is a value greater than or equal to 55%.

34. The method of claim 30, wherein the relatively high percentage of medium pores is a value greater than or equal to 60%.

35. The method of claim 30, wherein the heteropolyacid catalyst is prepared using an amount of an ammonium-containing compound sufficient to increase a percentage of medium pores in the heteropolyacid catalyst, where the ammonium-containing compound is selected from the group consisting of any ammonium compound that undergoes thermal decomposition to volatile components.

36. The method of claim 35, wherein the ammonium-containing compound is selected from the group consisting of ammonium hydroxide, ammonium nitrate, ammonium chloride, ammonium bromide, ammonium carbonate, ammonium salts of carboxylic acids, and mixtures or combinations thereof.

37. The method of claim 36, wherein the ammonium salts of carboxylic acids are selected from the group consisting of ammonium acetate, ammonium formate, ammonium propionate, ammonium butionate, and mixtures or combinations thereof.

38. The method of claim 1, where in the heteropolyacid catalyst composition comprises a compound having the general formula:

$$Mo_{12}P_aV_bCu_cBi_{d1}B_{d2}MII_eMIII_fO_g \qquad (IV)$$

where:
MII is selected from the group consisting of potassium (K), rubidium (Rb), cesium (Cs), thallium (Tl), and mixtures or combinations thereof,
MIII is selected from the group consisting of antimony (Sb), cerium (Ce), niobium (Nb), indium (In), iron (Fe), chromium (Cr), cobalt (Co), nickel (Ni), manganese (Mn), arsenic (As), silver (Ag), zinc (Zn), germanium (Ge), gallium (Ga), zirconium (Zr), magnesium (Mg), barium (Ba), lead (Pb), tin (Sn), titanium (Ti), aluminum (Al), silicon (Si), tantalum (Ta), tungsten (W), lanthanum (La), and mixtures or combinations thereof,
a is a number having a value between about 0.5 and about 3.5,
b is a number having a value between about 0.01 and about 5.0,
c is a number having a value between about 0.0 and about 1.5,
d1 is a number having a value between about 0.01 and about 2.0,
d2 is a number having a value between about 0.01 and about 5.0,
e is a number having a value between about 0.0 and about 5.0,
f is a number having a value between about 0.0 and about 5.0, and
g is a number having a value representing a sufficient number of oxygen atoms to balance the oxidation state of the heteropolyacid catalyst of formula (IV).

39. The method of claim 38, wherein the aldehyde feedstock comprises a mixture of isobutanal and methacrolein.

40. The method of claim 38, wherein the relatively high percentage of medium pores is a value between about 50% and about 80%.

41. The method of claim 38, wherein the relatively high percentage of medium pores is a value greater than or equal to 55%.

42. The method of claim 38, wherein the relatively high percentage of medium pores is a value greater than or equal to 60%.

43. The method of claim 38, wherein the heteropolyacid catalyst is prepared using an amount of an ammonium-containing compound sufficient to increase a percentage of medium pores in the heteropolyacid catalyst, where the ammonium-containing compound is selected from the group consisting of any ammonium compound that undergoes thermal decomposition to volatile components.

44. The method of claim 43, wherein the ammonium-containing compound is selected from the group consisting of ammonium hydroxide, ammonium nitrate, ammonium chloride, ammonium bromide, ammonium carbonate, ammonium salts of carboxylic acids, and mixtures or combinations thereof.

45. The method of claim 44, wherein the ammonium salts of carboxylic acids are selected from the group consisting of ammonium acetate, ammonium formate, ammonium propionate, ammonium butionate, and mixtures or combinations thereof.

46. The method of claim 1, wherein the aldehyde feedstock comprises a mixture of isobutanal and methacrolein ranging from about 5 wt. % isobutanal and about 95 wt. % methacrolein to from about 95 wt. % isobutanal and about 5 wt. % methacrolein.

47. The method of claim 1, wherein the aldehyde feedstock comprises a mixture of isobutanal and methacrolein ranging from about 10 wt. % isobutanal and about 90 wt. % methacrolein to about 90 wt. % isobutanal and about 10 wt. % methacrolein.

48. The method of claim 1, wherein the aldehyde feedstock comprises a mixture of isobutanal and methacrolein ranging from about 15 wt. % isobutanal and about 85 wt. % methacrolein to about 85 wt. % isobutanal and about 15 wt. % methacrolein.

49. The method of claim 1, wherein the aldehyde feedstock comprises a mixture of isobutanal and methacrolein ranging from about 20 wt. % isobutanal and about 80 wt. % methacrolein to about 80 wt. % isobutanal and about 20 wt. % methacrolein.

50. The method of claim 1, wherein the aldehyde feedstock comprises a mixture of isobutanal and methacrolein ranging from about 25 wt. % isobutanal and about 75 wt. % methacrolein to about 75 wt. % isobutanal and about 25 wt. % methacrolein.

51. The method of claim 1, wherein the aldehyde feedstock comprises a mixture of isobutanal and methacrolein ranging from about 30 wt. % isobutanal and about 70 wt. % methacrolein to about 70 wt. % isobutanal and about 30 wt. % methacrolein.

52. The method of claim 1, wherein the aldehyde feedstock comprises a mixture of isobutanal and methacrolein ranging from about 35 wt. % isobutanal and about 65 wt. % methacrolein to about 65 wt. % isobutanal and about 35 wt. % methacrolein.

53. The method of claim 1, wherein the aldehyde feedstock comprises a mixture of isobutanal and methacrolein ranging from about 40 wt. % isobutanal and about 60 wt. % methacrolein to about 60 wt. % isobutanal and about 40 wt. % methacrolein.

54. The method of claim 1, wherein the aldehyde feedstock comprises a mixture of isobutanal and methacrolein ranging from about 45 wt. % isobutanal and about 55 wt. % methacrolein to about 55 wt. % isobutanal and about 45 wt. % methacrolein.

55. The method of claim 1, wherein the aldehyde feedstock comprises a mixture of isobutanal and methacrolein ranging from about 50 wt. % isobutanal and about 50 wt. % methacrolein.

56. The method of claim 13, wherein the aldehyde feedstock comprises a mixture of isobutanal and methacrolein ranging from about 5 wt. % isobutanal and about 95 wt. % methacrolein to from about 95 wt. % isobutanal and about 5 wt. % methacrolein.

57. The method of claim 13, wherein the aldehyde feedstock comprises a mixture of isobutanal and methacrolein ranging from about 50 wt. % isobutanal and about 50 wt. % methacrolein.

58. The method of claim 22, wherein the aldehyde feedstock comprises a mixture of isobutanal and methacrolein ranging from about 5 wt. % isobutanal and about 95 wt. % methacrolein to from about 95 wt. % isobutanal and about 5 wt. % methacrolein.

59. The method of claim 22, wherein the aldehyde feedstock comprises a mixture of isobutanal and methacrolein ranging from about 50 wt. % isobutanal and about 50 wt. % methacrolein.

60. The method of claim 30, wherein the aldehyde feedstock comprises a mixture of isobutanal and methacrolein ranging from about 5 wt. % isobutanal and about 95 wt. % methacrolein to from about 95 wt. % isobutanal and about 5 wt. % methacrolein.

61. The method of claim 30, wherein the aldehyde feedstock comprises a mixture of isobutanal and methacrolein ranging from about 50 wt. % isobutanal and about 50 wt. % methacrolein.

62. The method of claim 38, wherein the aldehyde feedstock comprises a mixture of isobutanal and methacrolein ranging from about 5 wt. % isobutanal and about 95 wt. % methacrolein to from about 95 wt. % isobutanal and about 5 wt. % methacrolein.

63. The method of claim 38, wherein the aldehyde feedstock comprises a mixture of isobutanal and methacrolein ranging from about 50 wt. % isobutanal and about 50 wt. % methacrolein.

64. The method of claim 13, wherein the MI comprises bismuth.

65. The method of claim 13, wherein the MI comprises boron.

* * * * *